(12) United States Patent
Pusch et al.

(10) Patent No.: US 10,441,440 B2
(45) Date of Patent: Oct. 15, 2019

(54) PROSTHESIS WITH A PASSIVE RELEASE DEVICE

(71) Applicant: OTTO BOCK HEALTHCARE GMBH, Duderstadt (DE)

(72) Inventors: Martin Pusch, Duderstadt (DE); Sven Kaltenborn, Duderstadt (DE); Luder Mosler, Duderstadt (DE); Georg Gehrmann, Gottingen (DE); Carsten Monicke, Duderstadt (DE)

(73) Assignee: OTTOBOCK SE & CO. KGAA, Duderstadt (DE)

( * ) Notice: Subject to any disclaimer, the term of this patent is extended or adjusted under 35 U.S.C. 154(b) by 0 days.

(21) Appl. No.: 15/305,132

(22) PCT Filed: Apr. 29, 2015

(86) PCT No.: PCT/EP2015/059365
§ 371 (c)(1),
(2) Date: Oct. 19, 2016

(87) PCT Pub. No.: WO2015/165981
PCT Pub. Date: Nov. 5, 2015

(65) Prior Publication Data
US 2017/0042703 A1 Feb. 16, 2017

(30) Foreign Application Priority Data
Apr. 30, 2014 (DE) .................. 10 2014 006 228

(51) Int. Cl.
*A61F 2/66* (2006.01)
*A61F 2/74* (2006.01)
(Continued)

(52) U.S. Cl.
CPC .................. *A61F 2/68* (2013.01); *A61F 2/66* (2013.01); *A61F 2002/6818* (2013.01);
(Continued)

(58) Field of Classification Search
CPC ............. A61F 2/60; A61F 2/66; A61F 2/6607
See application file for complete search history.

(56) References Cited

U.S. PATENT DOCUMENTS 3,871,032 A * 3/1975 Karas ................... A61F 2/6607
623/26
4,662,486 A 5/1987 Stenberg
(Continued)

FOREIGN PATENT DOCUMENTS

CN 1492748 A 4/2004
CN 1946357 A 4/2007
(Continued)

OTHER PUBLICATIONS

PCT International Search Report for PCT International Patent Application No. PCT/EP2015/059365, dated Sep. 3, 2015.

*Primary Examiner* — Marcia L Watkins
(74) *Attorney, Agent, or Firm* — Holland & Hart LLP (57) ABSTRACT

A prosthesis with a lower limb attachment part, a foot part, a connection element with a joint function that connects the lower limb attachment part with the foot part, and a release device which can be brought into a locking position in which the foot part and the lower limb attachment part are connected to each other in a rotationally fixed manner at least relative to a dorsal extension movement, and into a release position in which the foot part can be rotated relative to the lower limb attachment part. The release device is designed to passively switch from the locking position into the release position when a variable which correlates to an ankle torque (M) in the connection element lies above a pre-set threshold.

20 Claims, 10 Drawing Sheets

(51) Int. Cl.
*A61F 2/76* (2006.01)
*A61F 2/68* (2006.01)

(52) U.S. Cl.
CPC ... *A61F 2002/6854* (2013.01); *A61F 2002/74* (2013.01); *A61F 2002/745* (2013.01); *A61F 2002/748* (2013.01); *A61F 2002/7645* (2013.01)

(56) References Cited

U.S. PATENT DOCUMENTS

| | | | |
|---|---|---|---|
| 6,440,173 | B1 | 8/2002 | Meyer |
| 8,574,312 | B2 | 11/2013 | Moser et al. |
| 8,709,097 | B2 | 4/2014 | Jonsson et al. |
| 2002/0169402 | A1 | 11/2002 | Hatton et al. |
| 2007/0043449 | A1 | 2/2007 | Herr et al. |
| 2009/0204229 | A1* | 8/2009 | Mosler ............... A61F 2/6607 623/26 |
| 2012/0153875 | A1 | 6/2012 | Glaister |
| 2013/0006386 | A1 | 1/2013 | Hansen et al. |
| 2014/0088730 | A1* | 3/2014 | Hansen et al. ....... A61F 2/6607 623/26 |

FOREIGN PATENT DOCUMENTS

| | | |
|---|---|---|
| CN | 1964682 A | 5/2007 |
| CN | 101437470 A | 5/2009 |
| CN | 102427778 A | 4/2012 |
| CN | 103271783 A | 9/2013 |
| JP | S61-222445 A | 10/1986 |
| JP | 2005-000500 A | 1/2005 |
| JP | 2010-512819 A | 4/2010 |
| WO | 9712567 A1 | 4/1997 |
| WO | 2008071975 A1 | 6/2008 |
| WO | 2014039885 A1 | 3/2014 |

* cited by examiner

PROSTHESIS WITH A PASSIVE RELEASE DEVICE

TECHNICAL FIELD

The invention relates to a prosthesis with (a) a lower limb attachment part, (b) a foot part, (c) a connection element with a joint function that connects the lower limb attachment part with the foot part in accordance with an ankle joint, and (d) a release device by means of which the foot part can be brought into a locking position in which the foot part and the lower limb attachment part are connected to each other in a rotationally fixed manner at least relative to a dorsal extension movement of the foot part relative to the lower limb attachment part, and into a release position, in which the foot part can be rotated relative to the lower limb attachment part.

BACKGROUND

A prosthesis of this type may be designed, for example, as a pure prosthetic foot or a knee-foot-prosthesis and serves as a replacement at least for the natural foot. It is particularly important to prevent patients with weak muscular and coordination skills from tripping. Some prostheses are known that contain a microprocessor that is connected to acceleration sensors and, using the signals from the acceleration sensors, determines in which phase of the gait cycle a patient is currently in. The production and maintenance of this type of prosthesis is complex, meaning that not all patients have access to such prostheses.

A prosthesis is described in U.S. Pat. No. 8,709,097 B2 with a microprocessor that, by means of sensor data, measures when the gait progression is far enough along that the joint must be released. The disadvantage of this type of prosthesis is the considerable effort required for its production and maintenance. A prosthesis is described in WO 2014/039 885 A1 which also has a microprocessor and a number of sensors to measure the progression. Threshold values can be stored in the control system, these threshold values then being used to control the actuators of the prosthesis. The production and maintenance of this type of system are also complex.

US 2013/0006386 describes a prosthetic foot that comprises a coupling. This coupling becomes blocked under load and is released when the load is relieved in order to enable an adjustment to gradients and inclines.

SUMMARY

The invention aims to suggest a prosthesis which leads to a lower probability of tripping and is easy to produce.

The invention solves the problem by an above-mentioned prosthesis whose release device is designed to switch, particularly passively, from the locking position into the release position when an ankle torque in the connection element lies above an adjustable torque threshold, which may also be described as a dorsal extension threshold.

The advantage of this type of prosthesis is that the patient can stand securely. When the wearer is standing, the ankle torque is low, this ankle torque lying below a torque threshold. For this reason, the release device is in the locking position and the patient will stand confidently on the prosthesis.

Once the patient begins to walk, the ankle torque exceeds the preset torque threshold and the release device moves into its release position. The foot part conducts a dorsal extension movement relative to the lower limb attachment part. In other words, the tip of the foot moves towards the patient's knee. In the following swing phase, the distance between the tip of the foot and the ground increases, which reduces the risk of tripping.

A further advantage is that, with the prosthesis according to the invention, it is easier to deal with inclining ramps. With inclining ramps, the distance between the prosthesis and the ground is reduced in the swing phase, which increases the risk of tripping. With the prosthesis according to the invention, the distance to the ground is increased. This reduces the risk of tripping when the patient walks up an inclining ramp. Furthermore, the dorsal extension position facilitates the ascent of ramps at the end of the step.

Within the scope of the present description, the term lower limb attachment part should be understood particularly to mean a device that is designed to be directly or indirectly mechanically connected to an artificial or natural lower limb. It is thus also possible, but not necessary, to have an artificial lower limb and/or an artificial knee joint that is connected to the lower limb attachment part such that it is non-detachable or detachable.

The foot part should be understood in particular to mean the part of the prosthesis that assumes the function of the human lower foot. In particular the foot part may comprise a foot shell, which lends the prosthesis the appearance of a natural foot. However, this type of foot shell is dispensable.

The connection element should be understood in particular to mean a connection between the lower limb connection part and the foot part that allows a relative movement of both components, this movement corresponding to a movement of natural foot. The connection element may comprise a swivel joint or be formed by a swivel joint that comprises a fixed axis of rotation. This position of the axis of rotation can be independent from the rotation angle of the swivel joint.

However, it is also possible for the connection element to have several partial joints and a momentary axis of rotation, meaning that the axis of rotation, by means of which the momentary rotation of the foot part relative to the lower limb attachment part can be calculated, changes over time and/or according to the progress of the movement in the gait cycle. It is also possible that the connection element is at least partially constructed as a flexure bearing. The majority of prostheses aim to imitate the natural progression of movement as closely as possible. As the human foot comprises several partial joints, many prostheses have a connection element that has an axis of rotation whose position varies over time. The invention relates to prostheses with these types of connection elements.

The ankle torque should be understood particularly to mean the torque that is calculated from the momentary lever arm and the force acting on the foot part, in each case in relation to the—where applicable, momentary—axis of rotation. The ankle torque is positive if a compressive force is present on the tip of the foot of the foot part. In other words, the ankle torque is positive for a force that pushes the foot part into a dorsal extension movement. For a force that pushes the foot part into a plantar flexion movement, the ankle torque is negative.

At the point when the foot part is in the locking position by means of the release device, the release device is also in its locking position. In line with this, the release device is then in its release position when the foot part is in the release position.

It is possible and represents a preferred embodiment if the release device also prevents a plantar flexion movement of the foot part when in the locking position. Alternatively, it is also possible that the release device enables a plantar flexion movement when in the locking position, in particular if the ankle torque falls short of a pre-set plantar flexion threshold that is smaller than zero. In other words, it represents a preferred embodiment if the foot part can carry out a plantar flexion movement when in the locking position if the ankle torque falls short of a plantar flexion threshold. The plantar flexion threshold preferably has a maximum value of one fifth, in particular a maximum of one tenth, of the dorsal extension threshold.

The feature that the release device can be brought into a release position, in which the foot part can be rotated relative to the lower limb attachment part, should be understood especially to mean that the release device allows a dorsal extension movement of the foot part relative to the lower limb attachment part when in the release position.

The feature that the foot part can be brought into a locking position by means of the release device, in which the foot part and the lower limb attachment part are connected to each other in a rotationally fixed manner at least relative to a dorsal extension movement, should be especially understood to mean that the release device, when in the locking position, prevents a dorsal extension movement, as long as the set ankle torque does not exceed the threshold.

The feature that the release device is designed to switch from the locking position into the release position when a variable which correlates to an ankle torque in the connection element lies above a pre-set threshold should be understood especially to mean that the release device is designed in such a way that a considerable dorsal extension movement of the foot part is only effected if the threshold is exceeded. It is possible that the foot part may carry out a dorsal extension movement if the release device is in the locking position, yet this dorsal extension movement is so impeded that the patient barely notices it, or they do not notice it at all.

According to a preferred embodiment, a plantar flexion movement beyond the zero position is blocked.

The feature that the foot part can be rotated relative to the lower limb attachment part should be understood especially to mean that the release device obstructs a movement between the foot part and the lower limb attachment part to such a small degree that the foot part carries out or can carry out a dorsal extension movement in the normal gait cycle. The release device is preferably designed such that, when in the locking position, it produces a resistance that is at least three times as great against a movement of the foot part relative to the lower limb attachment part than when in the release position.

The connection element preferably connects the lower limb attachment part to the foot part in the same way an ankle joint does. This should be understood particularly to mean that the connection element imitates the movement of the human ankle joint. Therefore, the connection element may refer to a swivel joint; however, this is not necessary.

The connection element is designed in such a way that it produces a resistance against a dorsal extension and/or plantar flexion movement that is smaller, in particular at least 10 times smaller, than against a medial or lateral movement.

The feature that the release device is designed to passively switch from the locking position into the release position should be understood especially to mean that the switching occurs without an actuator. An actuator is a component that can be externally controlled to move another component through the application of energy. In other words, the passive switching refers to a change from the locking position into the release position, which occurs without the supply of stored and/or electrical energy. It is possible, but not necessary, that a switching status of a component, for example a valve, is changed upon switching. It is also possible that the switching occurs by a component not carrying out a movement until the pre-set torque threshold is exceeded; below this torque threshold, the component is rigid. For example, the release device may comprise a spring that is pre-loaded against an end stop.

It is possible, yet not necessary, for the threshold for the ankle torque to be known as a torque. In particular, it is possible that this torque threshold can be changed to greater and/or smaller torque thresholds without knowing the absolute value of the torque. The size of the respective torque threshold in Newton meters may therefore be known but it is not necessary.

The torque threshold may be determined in particular by exerting a vertically acting force on the lower limb attachment part, then tilting the lower limb attachment part according to the linear inclination in the gait cycle and recording the point in which the prosthesis exerts the force onto the floor. The (outermost) vector product (cross product) from the force and the lever arm—at the point at which the release device switches from the locking position into the release position—corresponds to the threshold.

The release device may be arranged parallel or serially to a further spring element of the prosthesis. For example, the spring element is part of the foot part. The spring element preferably comprises a carbon spring. A parallel arrangement should be understood to mean that the mechanical resistances of the release device and the spring element add up. A serial arrangement should be understood to mean that the spring travel of the release device and the spring element add up.

The release device may be arranged to be pressurised or tensile loaded. If the release device is pressurised, it is compressed at the end of the standing phase. If the release device is tensile loaded, it is uncompressed at the end of the standing phase.

According to a preferred embodiment, the prosthesis has a mechanical pre-loading device by means of which the foot part is pre-loaded in the dorsal extension position, for example a pre-load spring that may be arranged such that it is ready to operate upon the heel impact.

If the prosthesis does not have a pre-load spring, which is also a preferred embodiment, the release device is brought into its neutral position by the plantar flexion upon the heel impact. During the consequent dorsal extension, the pre-load spring supports the dorsal extension movement of the foot part.

According to a preferred embodiment, the release device is designed such that an ankle torque, which lies above the torque threshold, moves the foot part into a dorsal extension position and that during a swing phase in which no external torque is acting on the prosthesis, the foot part remains at least predominantly in the dorsal extension position. Should the patient walk with this prosthesis, a dorsal extension of the foot part relative to the lower limb attachment part will occur during the terminal standing phase in the gait cycle. In the following swing phase, the rotation position of the foot part relative to the lower limb attachment part does not change, or does so by an inconsiderable degree.

The feature that the rotation position does not fundamentally change should be understood to mean that, during the swing phase, a maximum of one third of the rotation path out of the dorsal extension position is covered. An especially large distance between the tip of the foot and the ground and thus a particularly low probability of tripping is then achieved when the foot part, in the swing phase, moves by a particularly small degree relative to the lower limb attachment part.

The release device (a) preferably comprises a hydraulic cylinder, which has a piston rod and a cylinder housing, and whose one end is connected to the foot part and whose other end is connected to the lower limb attachment part, and (b) which comprises a restraint device that can be brought into a closing position in which it prevents a movement of the piston rod, and into a opening position in which it enables the movement of the piston rod. The release device contains a hydraulic fluid, in particular a hydraulic liquid. The restraint device preferably comprises a check valve.

According to a preferred embodiment, the restraint device comprises a check valve, in particular an excess pressure non-return valve and/or a sequence valve which, when in the closing position, prevents a movement of the piston rod that leads to a dorsal extension movement of the foot part and to a plantar flexion movement of the foot part, and that enables the dorsal extension movement of the piston rod when in an opening position and that has an opening pressure $p_{open}$ at which the check valve moves out of the closing position into the opening position. This type of prosthesis is simple to construct and also quiet during operation.

According to a preferred embodiment, the check valve is designed in such a way that the torque threshold can be set based on the opening pressure of the check valve, in particular of the excess pressure non-return valve, at which the check valve moves out of the closing position into the opening position. In other words, the check valve may have an opening pressure adjustment device to set the opening pressure. The resulting release device is simple and robust. The additional advantage is that the torque threshold can be easily changed. The check valve should be understood to mean a device that enables the flow of the hydraulic fluid in precisely one flow direction.

According a preferred embodiment, the restraint device comprises a mechanical restraint element. The restraint element impedes a movement of the foot part as long as the ankle torque lies below the pre-set threshold. For example, the restraint element is designed to positively engage with a recess. The restraint element can preferably be set in its position such that the angle setting between the foot part and lower limb attachment part at which the restraint element impedes can be adjusted. In this way, by adjusting the restraint element, a change in the heel height of a shoe that is worn with the prosthesis may be compensated.

It is beneficial if the release device has a restraint structure and a spring, the restraint structure interacting with the restraint element in such a way that a movement of the foot part beyond the zero position is only possible against the resistance of a spring. This results in a mechanically simple prosthetic foot that has a low risk of tripping.

According to a preferred embodiment, the release device comprises a mechanical return element, a coupling ring and a brake that are connected with one another in such a way that when the foot part carries out a dorsal extension movement, the return element engages with the coupling ring such that the brake brakes the dorsal extension movement, and that when the foot part carries out a plantar flexion movement, the brake does not brake the plantar flexion movement, or does so less strongly than the dorsal extension movement. This reduces the risk of tripping and still impedes the resetting plantar flexion movement less or not at all.

The prosthesis preferably has a neutral position that is an angle setting of the foot part relative to the lower limb attachment part and in which the release device is in the locking position. This neutral position corresponds to the position that the foot part assumes if the patient wearing the prosthesis is standing.

The foot part is preferably positioned to the lower limb attachment part in such a way that a positive ankle torque is present on the foot part when in the neutral position.

The restraint device is preferably designed such that a plantar flexion movement is possible at least in an angular position of the foot part, this position lying between the neutral position and a maximum dorsally extended position. The release device is preferably designed such that, for this plantar flexion movement, an ankle torque is required that corresponds to a maximum of a fifth, in particular a maximum of a tenth, of the dorsal extension threshold according to feature (e) in claim 1.

It is beneficial if the restraint device comprises a second check valve that prevents a plantar flexion movement of the foot part when in a closing position and enables a plantar flexion movement of the foot part when in an opening position, and has a plantar flexion opening pressure at which the second check valve moves out of the closing position into the opening position.

The second check valve is preferably switched so that it counteracts the first check valve. This should understood to mean that hydraulic fluid can flow either through the first check valve or through the second check valve, but not through both at the same time.

According to a preferred embodiment, the hydraulic cylinder is designed to be double-acting and is connected to the restraint device in such a way that a dorsal extension movement of the foot part only effects a flow of hydraulic fluid through the first check valve and a plantar flexion movement of the foot part only effects a flow of hydraulic fluid through the second check valve. This results in a simply constructed prosthesis.

Alternatively, the release device comprises a second hydraulic cylinder which has a second piston rod and a second cylinder housing, and whose one end is connected to the foot part and whose other end is connected to the lower limb attachment part, the second hydraulic cylinder being connected to the restraint device and the first hydraulic cylinder such that a dorsal extension movement of the foot part effects a flow of hydraulic fluid from the second hydraulic cylinder, through the first check valve and into the first hydraulic cylinder, and that a plantar flexion movement of the foot part effects a flow of hydraulic fluid from the first hydraulic cylinder, through the second check valve and into the second hydraulic cylinder. When the foot part is moving, this results in a rotation about an axis of rotation that lies between the hydraulic cylinders: a physical swivel joint is not necessary.

The release device preferably comprises a magnetorheological fluid and/or an electrorheological fluid. For example, the hydraulic cylinder in which the magentorheological fluid and/or electroheological fluid is arranged comprises a permanent magnet which keeps the fluid in its highly viscous state, such that a movement of the piston in the hydraulic cylinder is prevented until a pre-set force acting on the piston is exceeded. If the force acting on the piston is exceeded, the piston continues to move in a damped manner.

According to a preferred embodiment, the release device comprises a damping device, by means of which a dorsal extension movement and/or a plantar flexion movement of the connection element can be damped. The term damping should be understood to mean that a resetting force is applied against the ankle torque that effects the dorsal extension movement of the foot part relative to the lower limb attachment part. As the damping device induces a resetting force, the damping device acts as a time delay component. It is possible that the damping device comprises two or more damping elements, such as throttles.

The damping device is preferably designed for at least predominantly dissipative damping; this means that at least 50% of the energy that is introduced into the damping device shall be converted into heat. If the release device has one hydraulic cylinder, the damping device may comprise a throttle, for example. It is especially beneficial if the damping device conducts changeable damping. Should the damping device have a throttle, it is preferably an adjustable throttle.

According to a preferred embodiment, the foot part can be brought into a neutral position, in which a person wearing the prosthesis is standing, relative to the lower limb attachment part and into a dorsal extension position, in which a tip of the foot of the foot part forms a smaller angle with the lower limb attachment part than when in the neutral position, the prosthesis comprising a mechanical pre-loading device by means of which the foot part is pre-loaded in the dorsal extension position. This pre-loading device may comprise a spring, for example. The pre-loading device is especially constructed in such a way that it cannot move the foot part as long as the release device is in the locking position. If the release device then moves into its release position, the pre-loading device supports the dorsal extension movement of the foot part, thereby ensuring that the tip of the foot is always a large distance from the ground.

The damping device is preferably configured to (also) dampen the plantar flexion movement of the foot part. It is favourable if the damping of the plantar flexion movement is smaller than the damping of the dorsal extension movement. This causes the foot part to move quickly into its neutral position upon heel contact at the beginning of the gait cycle. This encourages a fluid progression of movement.

The torque threshold is preferably selected such that the release device is always in the locking position when standing. For example, the torque threshold depends on the body weight of the patient and, upon the mounting of the prosthesis, is determined by means of successive amendments to the torque threshold and walking tests.

The prosthesis preferably refers to a prosthetic foot, meaning that it does not have an artificial knee joint. In this case, the passive switching from the locking position into the release position is especially advantageous, as there are no measurements available with which the point in the gait cycle can also be concluded.

It is beneficial if the prosthesis is designed to conduct a dorsal extension movement of at least 3°, thereby achieving a sufficiently large distance from the ground. It is also advantageous if the dorsal extension movement has a maximum value of 6°. This prevents too great a loss of energy whilst walking and too great a buckling of the foot.

The variable which correlates to an ankle torque in the connection element may also be understood to mean the point of force application in the foot part. If the patient rolls on to the forefoot, the point of application of the (weight) force shifts to the forefoot. On a healthy individual, this is detected by bending in the toe area.

The invention also solves the problem by means of an adapter that is designed to be assembled in a prosthesis which comprises a lower limb attachment part, a foot part and a connection element with a joint function that connects the lower limb attachment part with the foot part. The adapter has a release device, by means of which the foot part can be brought into a locking position, in which the foot part and the lower limb attachment part are connected to each other in a rotationally fixed manner, and into a release position, in which the foot part can be rotated relative to the lower limb attachment part, the release device being designed to switch from the locking position into the release position when a variable which correlates to an ankle torque in the connection element lies above a pre-set threshold. This type of adapter may also be used parallel to a hydraulic and/or mechatronic control system of the prosthesis, if available.

BRIEF DESCRIPTION OF THE DRAWINGS

In the following, the invention will be explained in more detail in the attached drawings. They show FIG. 1 a first embodiment of a prosthesis according to the invention according to a first embodiment:

FIG. 2 in the partial FIGS. 2a, 2b and 2c, a possible embodiment of a release device and in the partial FIG. 2d, the progression of the ankle torque over the course of the gait cycle;

FIG. 3 with the partial FIGS. 3a and 3b, a second embodiment of a prosthesis according to the invention;

FIG. 4 in the partial FIG. 4a, a third embodiment of a prosthesis according to the invention, and in the partial FIGS. 4b and 4c, a circuit diagram of the accompanying release device;

DETAILED DESCRIPTION

Figure 1:
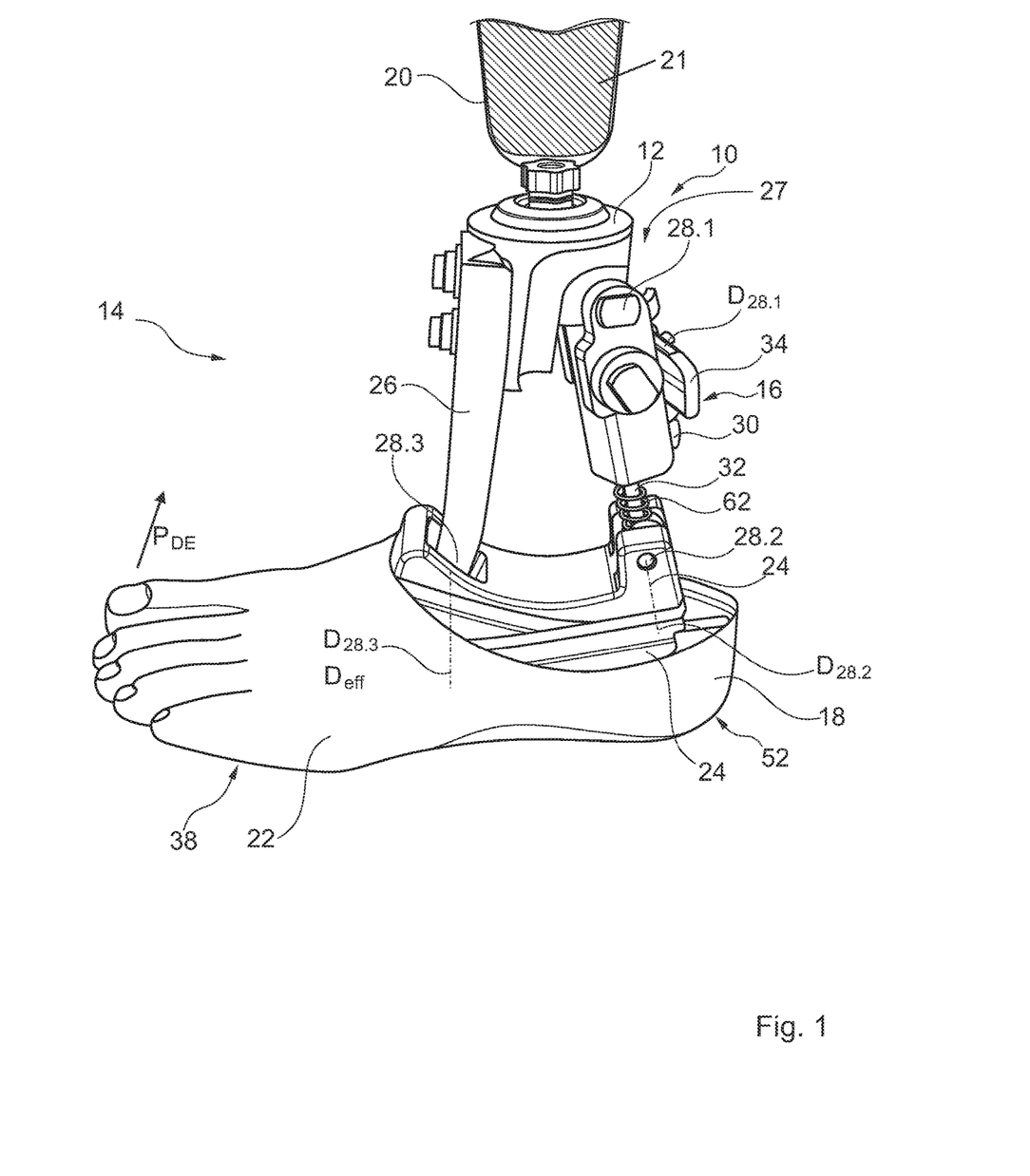

FIG. 1 depicts a prosthesis 10 according to the invention with a lower limb attachment part 12, a connection element 14, a release device 16 and a foot part 18. The foot part 18 is connected to the lower limb attachment part 12 via the connection element 14. The lower limb attachment part 12 is designed to connect to a schematically depicted lower limb accommodation 20.

The foot part 18 comprises a foot shell 22, which lends the prosthesis 10 a natural appearance. The foot part also has a base plate 24 onto which the foot shell 22 and the connection element 14 are fixed.

In the present case, the connection element 14 comprises a rigid arm 26 that is centrally fixed to the foot part 18. The release device 16 forms a second arm 27, the length of which is adjustable and that is fixed to a heel section of the prosthesis 10 on the foot part 18.

FIG. 1 shows that the connection element 14 has three partial joints 28.1, 28.2, 28.2, which are all swivel joints and each comprise axes of rotation $D_{28.1}$, $D_{28.2}$ and $D_{28.3}$.

When the prosthesis 10 moves, the foot part 18 rotates relative to the lower limb attachment part 12 about an axis of rotation $D_{eff}$.

The release device 16 comprises a hydraulic cylinder 30 that has a piston rod 32 and a cylinder housing 34. The hydraulic cylinder 30 is connected to the lower limb attachment part 12 at its one end in the partial joint 28.1. The hydraulic cylinder 30 is connected to the foot part 18 at its other end via the partial joint 28.2.

Figure 2A:
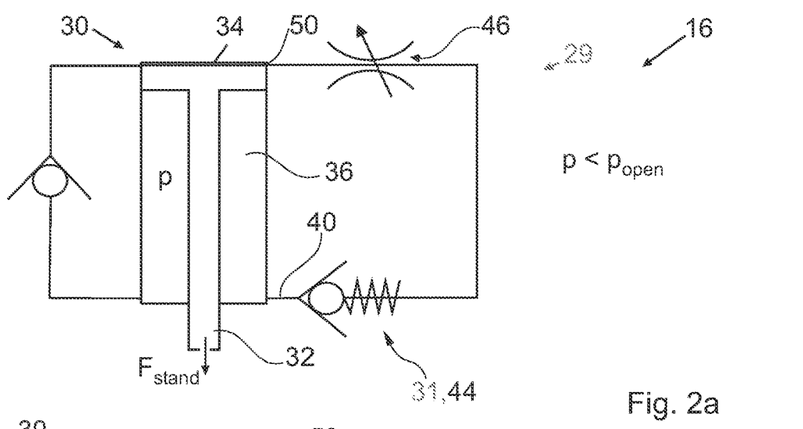

FIG. 2a shows a schematic depiction of the release device 16. The release device 16 comprises a restraint device 29, which is connected to the hydraulic cylinder 30. It should be recognised that the piston rod 32 of the hydraulic cylinder 30 runs within a cylinder housing 34 that is filled with a fluid 36, in particular a hydraulic fluid. If the prosthesis 10 is in the standing position, as depicted in FIG. 1, a standing force $F_{stand}$ acts on the piston rod 32, which, in this position, is inserted as far as possible into the cylinder housing 34. In this state, the release device 16 is rigid. The restraint device 29 and therefore the release device 16 are in a closing position, in which the piston rod 32 cannot move.

In the middle standing phase, an increasing force occurs on one ball area 38 (see FIG. 1) of the prosthesis 10. This results in an ankle torque $\vec{M}$ about the axis of rotation $D_{28.3}$. This causes the force F acting on the piston rod 32 to reduce and eventually become negative and the piston rod 32 to be subjected to a tensile load. This results in an increase in pressure p in the cylinder housing 34.

The restraint device 29 has an outlet 40 that is connected to an interior 42 of the cylinder housing 34, and a check valve 31, which is formed by an excess pressure non-return valve 44 in the present case. The outlet 40 may also comprise an adjustable throttle 46 and, in the cylinder housing 34, ends in an outflow opening 50. An inflow opening 48 of the outlet 40 is separated from an outflow opening 50 by the piston rod 32.

Upon progression in the gait cycle, the ankle torque $\vec{M}$ that the foot part 18 and the lower limb attachment part 12 exert on the connection element 14 increases continuously. This causes the force F, which is acting on the piston rod 32, to decrease until it reaches a value of zero. A negative force $F_{DE}$, i.e. a tensile force, then comes into effect on the piston rod 32.

Figure 2B:
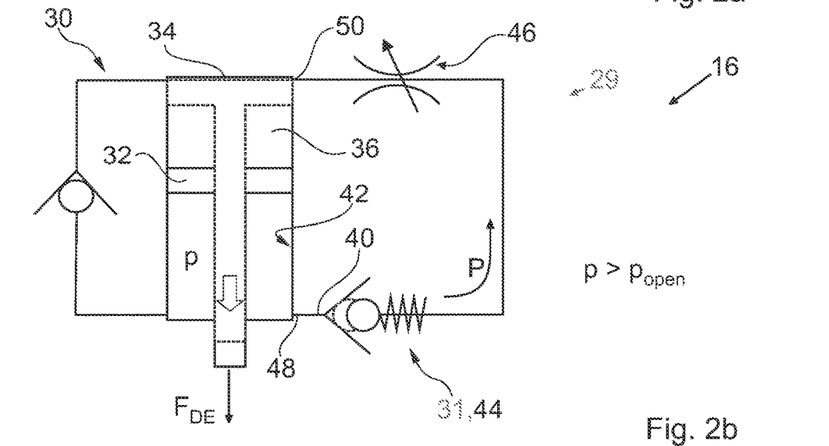

FIG. 2b shows that this results in an increase in the pressure p on the inflow opening 48. As soon as the pressure p is greater than an opening pressure $p_{open}$ of the excess pressure non-return valve 44, it will open and fluid 36 flows, as indicated by the arrow P, towards the outflow opening 50. In other words, the restraint device 29 is in the opening position. This results in a movement of the piston rod 32 in the cylinder housing 34 and causes a dorsal extension movement, which is indicated in FIG. 1 by the arrow $P_{DE}$. Via the adjustable throttle 46, the flow of the fluid 36 through the outlet 40 is damped in such a way that a sequence of movement that is more comfortable for the patient is obtained. In other words, there is an additional movement of the foot part which creates a greater ground clearance and which is maintained in the swing phase.

Figure 2C:
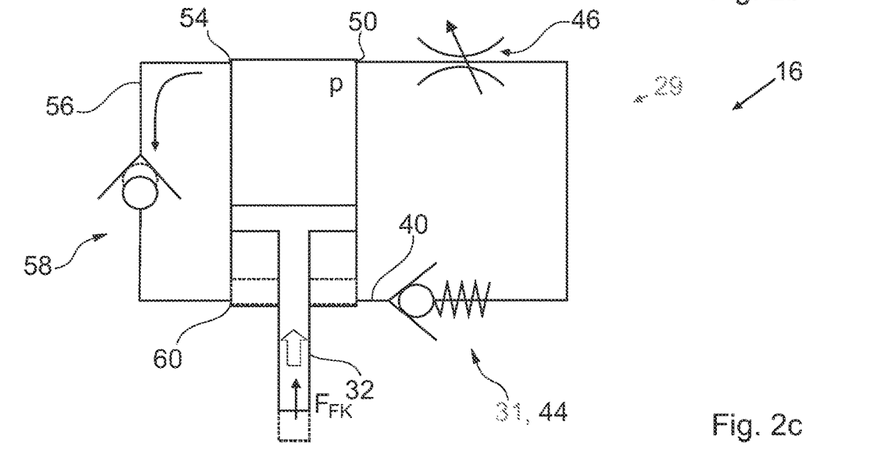

The dotted line in FIG. 2c depicts the piston rod 32 in its position at the end of the standing phase.

It is possible and represents a preferred embodiment that the prosthesis comprises a return spring, which brings the foot part, when in the swing phase, back into its neutral position, i.e. the position held when standing.

In the swing phase, the foot part 18 has no contact with the ground. If the prosthesis—as in the above embodiment—does not have a return spring, the piston rod 32 does not move relative to the cylinder housing 34.

The end of the swing phase is followed by the standing phase, when a heel section 52 of the prosthesis 10 makes contact with the ground. This causes a compressive force $F_{FK}$ to act on the piston rod 32. FIG. 2c shows that the pressure p increases on the outflow opening 50, yet the fluid 36 cannot flow away through the outlet 40, as the excess pressure non-return valve 44 blocks it. The fluid 36 flows through an inflow opening 54 of a return channel 56 through a second check valve 46, in the present case formed by a non-return valve, towards a return flow opening 60, so that the piston rod 32 can move back into its initial position, depicted in FIG. 2a.

Figure 2D:
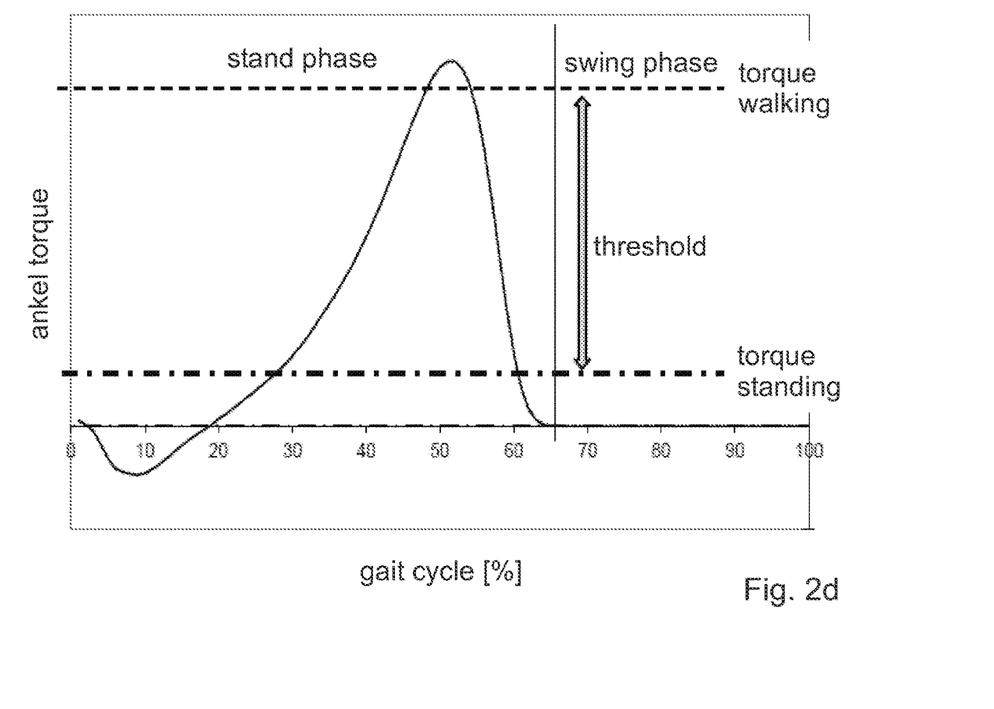

FIG. 2d shows the progression of the ankle torque M in arbitrary units of progress in the gait cycle. It should be noted that any ankle torque M that is greater than the ankle torque M when standing can be selected as a threshold. In order to set the threshold, the ankle torque M is recorded, for example, when standing and then the ankle torque M is set to be larger. It is then determined whether this threshold is small enough to obtain the release position in the gait cycle.

FIG. 1 shows that the prosthesis 10 may comprise a pre-loading device 62, which is formed by the compression spring in the present case. The pre-loading device 62 exerts a pre-load force on the foot part 18, which pre-loads the foot part 18 into a dorsal extension position.

According to an alternative embodiment, the pre-loading device 62 is formed by a tension spring, which pre-loads the foot part 18 into a plantar extension position.

Figure 3A:
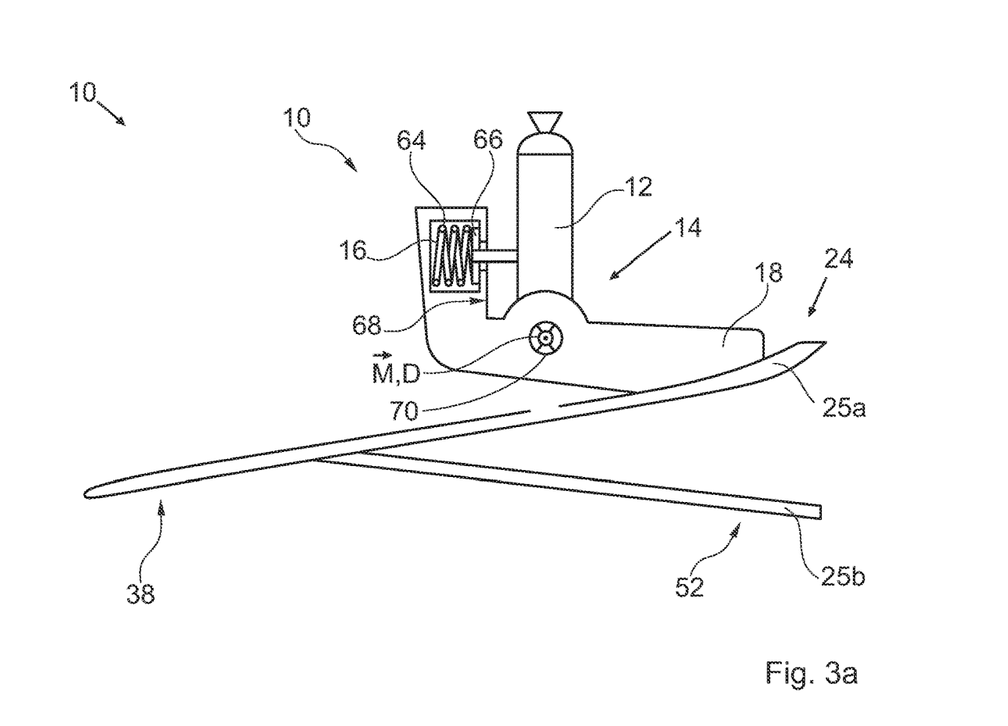
Figure 3B:
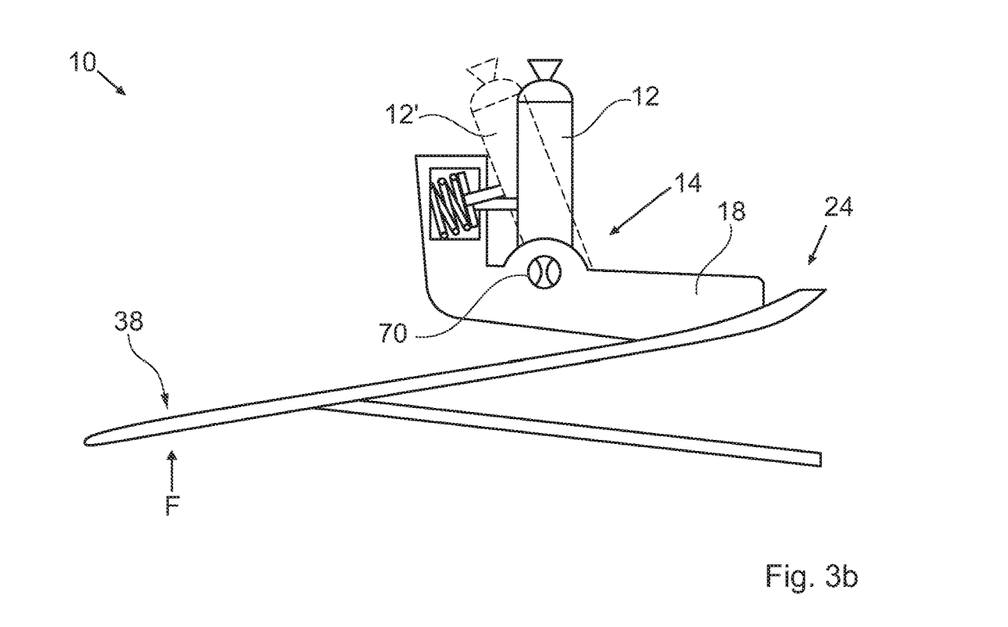

FIG. 3, with the partial FIGS. 3a and 3b, depicts a second embodiment of a prosthesis 10 according to the invention. The base plate 24 comprises two spring elements 25a, 25b, for example made of carbon fibres, that are fixed to one another. The release device 16 is arranged serially in relation to the spring elements 25a, 25b and it is tensile loaded. The release device 16 comprises a captured compression spring 64 that pre-loads a plate 66 against an end stop 68. In the present case, the end stop 68 is formed by the wall of a cage of the compression spring 64. FIG. 3a depicts the state when standing.

FIG. 3b depicts the state at the end of the standing phase. As the result of a force F on the ball area 38, the ankle torque M increases so much that the plate 66 releases itself from the end stop 68 and compresses it against the force of the compression spring 64. This causes the foot part 18 to move into the dorsally extending position. In FIG. 3b, this is depicted by the dotted lower limb attachment part 12'.

The prosthesis 10 comprises a damping device 70 that dampens a reset movement, which is at least also effected by the compression spring 64.

Figure 4A:
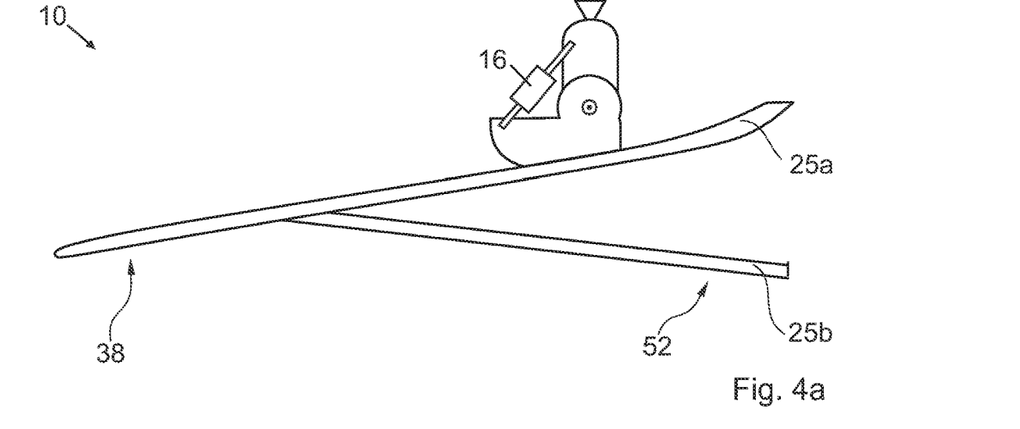

FIG. 4a shows a prosthesis whose schematically depicted release device 16 is arranged serially in relation to the spring elements 25a, 25b. The release device 16 is pressurised.

Figure 4B:
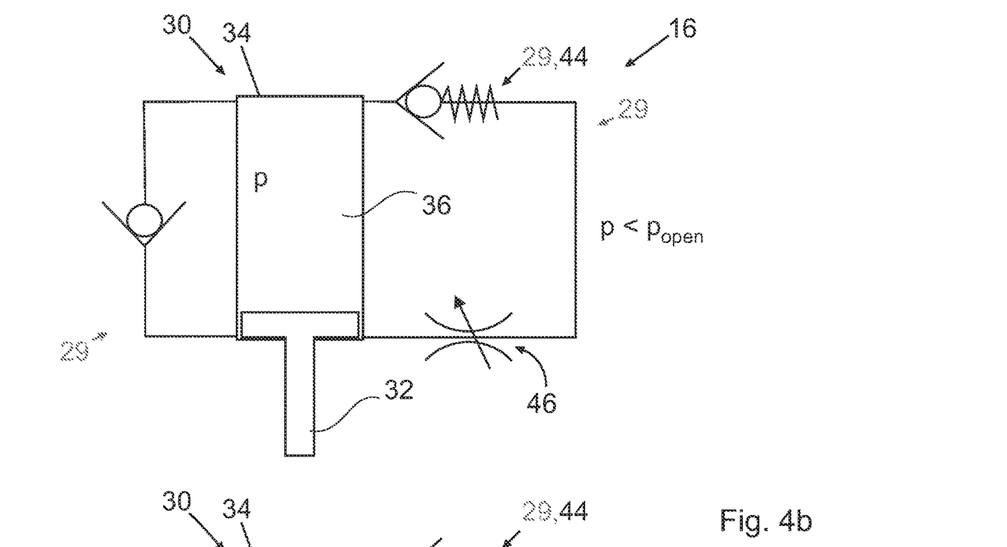

FIG. 4b shows the position of the release device 16 in the standing phase. The piston rod 32 is on the end stop in the cylinder housing 34, the pressure p is smaller than the opening pressure $p_{open}$ and the release device 16 is rigid. The restraint device 29 is in the closing position.

Figure 4C:
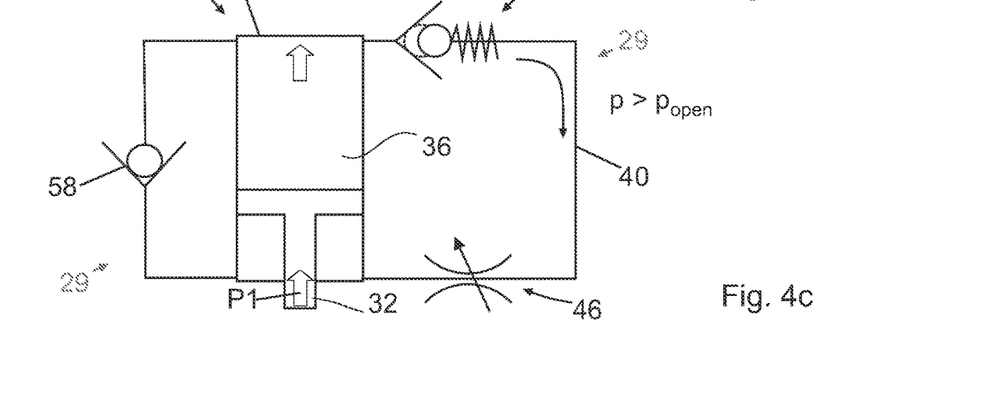

FIG. 4c shows the movement of the piston rod 32 when the pressure p exceeds the opening pressure $p_{open}$. The fluid 36 flows through the outlet 40 and the throttle 46. The restraint device 29 is in the opening position.

Upon heel impact, the piston rod 32 moves against the arrow P1, i.e. downwards in FIG. 4c, and the non-return valve 58 opens, whereas the excess pressure non-return valve 44 closes.

Figure 5:
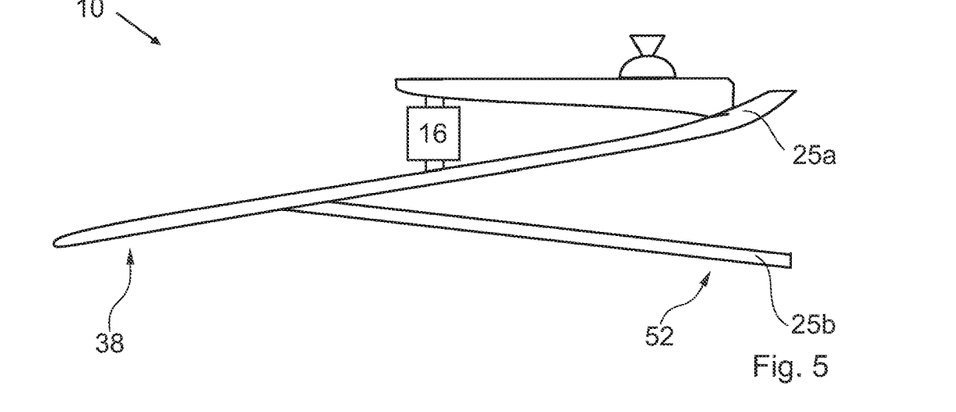
FIG. 5 a fourth embodiment of a prosthesis according to the invention.

FIG. 5 shows a prosthesis 10 whose schematically depicted release device 16 is pressurised and arranged to operate parallel to the spring elements 25a, 25b.

Figure 6:
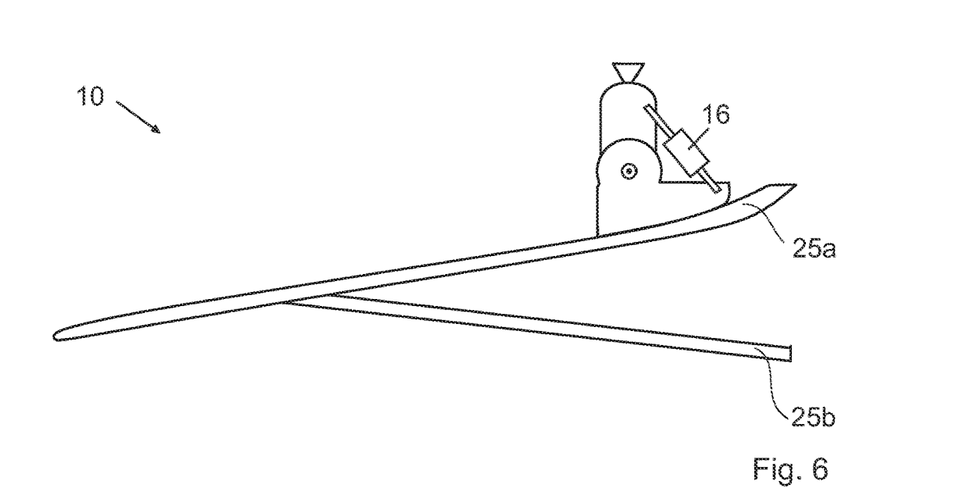
FIG. 6 a fifth embodiment of a prosthesis according to the invention.

FIG. 6 shows a prosthesis 10 whose schematically depicted release device 16 is tensile loaded and arranged to operate serially in relation to the spring elements 25a, 25b.

Figure 7:
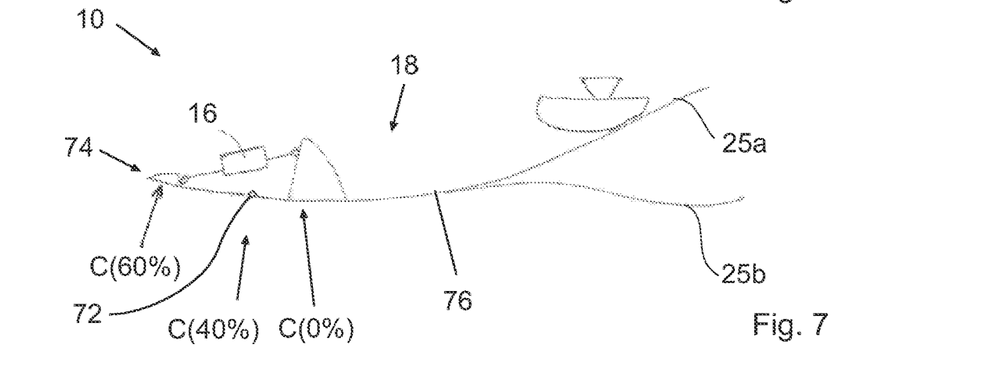
FIG. 7 depicts a sixth embodiment of a prosthesis according to the invention that is switched by means of the body's centre of gravity, and FIG. 8 the progression of the force of the ankle torque over the course of the gait cycle.

FIG. 7 depicts a prosthesis 10 whose release device 16 is designed to switch from the locking position into the release position if the position of the projection of the body's centre of gravity onto the foot part exceeds a pre-set threshold. In the gait cycle, the body's centre of gravity C moves in percent depending on the progress in the gait cycle.

It should be recognised that the foot part 18 comprises a forefoot joint 72, which connects a tip of the foot 74 to a midfoot part 76. The release device 16 spans the forefoot joint 72 and is fixed to the tip of the foot 74 on the one side and to the midfoot part 76 on the other.

At the beginning of the gait cycle, the projection C of the body's centre of gravity lies in the midfoot part 76 and moves towards the foot part 18. As soon as the projection C of the body's centre of gravity has reached the forefoot 72, in the present case 40% of the way through the gait cycle, the release device 16 is subjected to pressure. Once the opening pressure has been exceeded, the release device 16 moves into the release position and the tip of the foot 74 moves towards the midfoot part 76. This remains as such in the swing phase and creates more ground clearance.

Figure 8:
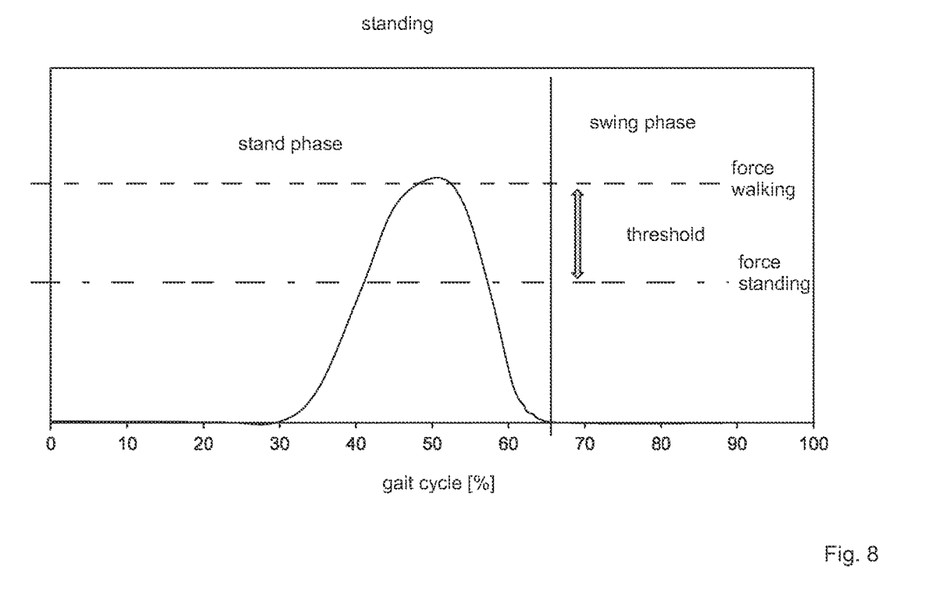

FIG. 8 shows the progression of the force K in arbitrary units of progress in the gait cycle. It should be noted that any force K that is greater than the force K when standing can be selected as a threshold. In order to set the threshold, force K is recorded, for example, when standing and then the force K is set to be larger. It is then determined whether this threshold is small enough to obtain the release position in the gait cycle. In addition, it is preferably determined whether the threshold is sufficiently large to enable a stable standing position.

As an alternative embodiment in FIG. 5, the release device 16 may be an element that is controlled via the force progression from FIG. 8, which switches an adjustable threshold of the force K when it is exceeded. In this embodiment, the force K is a force that results from the weight force of the patient.

Figure 9:
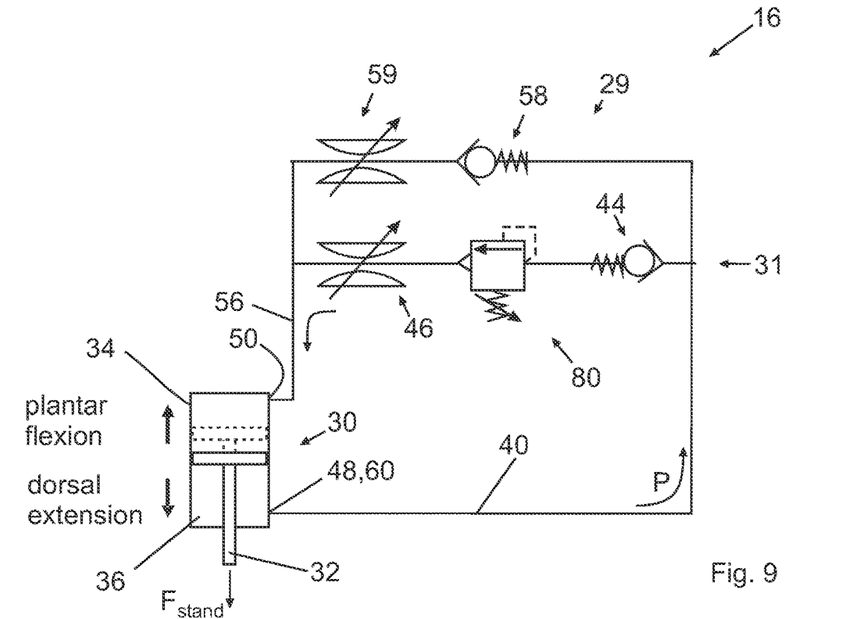
FIG. 9 shows the release device of a seventh embodiment of a prosthesis according to the invention whose check valve comprises a sequence valve.

FIG. 9 depicts a release device 16 for a prosthesis according to the invention whose check valve 31 comprises a sequence valve 80, alongside a non-return valve 44. FIG. 9 also shows that the release device 16 has a damping device 59.

If the foot part carries out a dorsal extension movement and when the ankle torque exceeds the dorsal extension threshold, the hydraulic fluid flows out of the opening 48, through the first check valve 31 and through the opening 50 back into the hydraulic cylinder 34 into a space that is separated from the space connected to the opening 48 by means of the piston of the hydraulic cylinder 34. If the foot part carries out a plantar flexion movement, the hydraulic fluid flows out of the opening 50, through the second check valve 58 and back through the opening 48 into the hydraulic cylinder 34.

Figure 10:
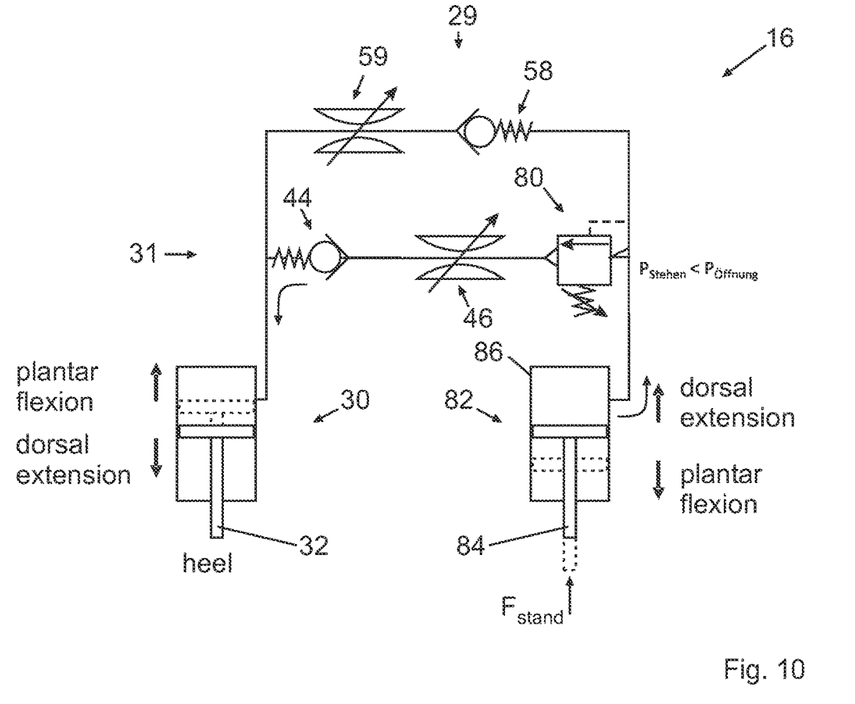
FIG. 10 shows the release device of an eighth embodiment of a prosthesis according to the invention whose release device comprises two hydraulic cylinders.

FIG. 10 shows an embodiment whose release device 16 comprises a second hydraulic cylinder 82, which has a second piston rod 84 and a second cylinder housing 86 and which is connected to the first cylinder 30 in such a way that an insertion of the second piston rod 84 into the second cylinder housing 86 causes the first piston rod 32 to be pushed out of the first cylinder housing 34.

The second hydraulic cylinder 82 is preferably arranged such that it replaces the rigid arm 26 (see FIG. 1). In this case, the second piston rod 84 in the partial joint 28.3 is connected to the foot part 18, especially to the base plate 24.

Should the foot part carry out a dorsal extension movement and if the ankle torque exceeds the dorsal extension threshold, the hydraulic fluid flows out of the second hydraulic cylinder 82, through the first check valve 31 only and into the first hydraulic cylinder 30. Should the foot part carry out a plantar flexion movement, the hydraulic fluid flows out of the first hydraulic cylinder 30, through the second check valve 58 only and into the second hydraulic cylinder 34.

Figure 11:
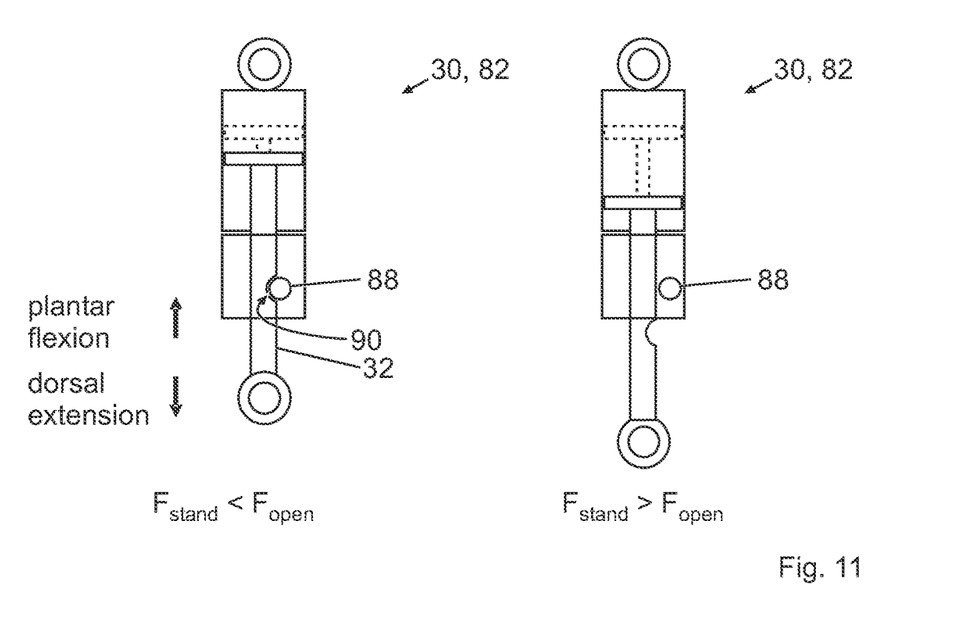
FIG. 11 shows the release device of a ninth embodiment of a prosthesis according to the invention whose restraint device comprises a mechanical restraint element.

FIG. 11 depicts an alternative embodiment for the first hydraulic cylinder 30 or, if present, the second hydraulic cylinder 82. It should be noted that the hydraulic cylinder 30 comprises a restraint device which, in the present case, may be formed by a pin or a bolt. The element 88 interacts positively with a recess 90, thereby impeding a movement of the piston rod 32. If the prosthesis only comprises a single hydraulic cylinder, the element ensures that the foot part 18 (see FIG. 1) cannot swivel relative to the lower limb attachment part 20, as long as the torque on the foot part is sufficiently small.

The right-hand partial image depicts the situation in which the ankle torque has exceeded the threshold, which has caused the restraint element 88 to slip out of the recess 90. The piston rod 32 can now move freely. It is favourable for the restraint element 88 to be pre-loaded on the recess 90, for example by means of a spring. Alternatively or additionally, it is possible that the restraint element 88 is spring-mounted. The shape of the restraint element 88 and the recess 90, and the force with which the restraint element 88 is pressed into the recess 90, influence the threshold at which the foot part can carry out a dorsal extension movement.

Figure 12:
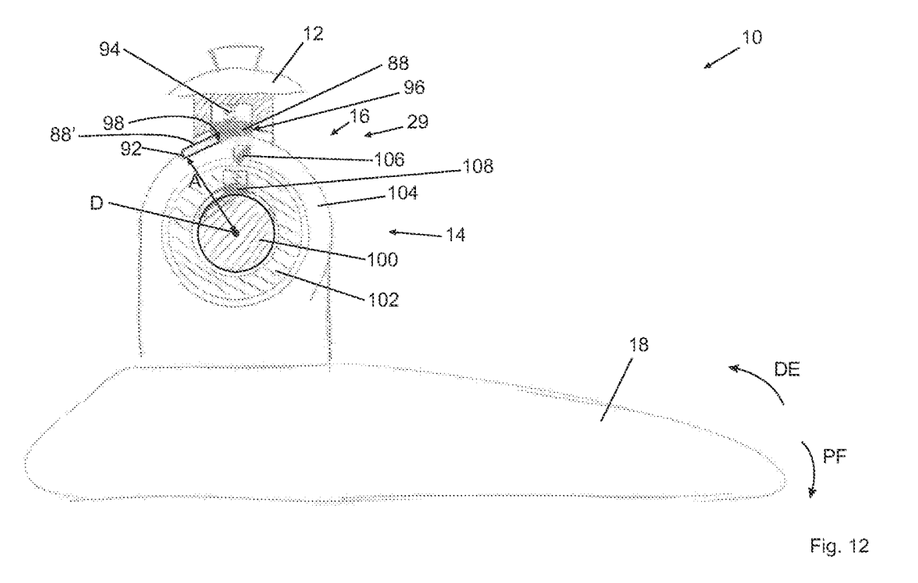
FIG. 12 depicts another embodiment of a prosthesis according to the invention, wherein the mechanical restraint element 88 of the release device 16 is designed as a sliding element that interacts with a restraint structure 92.

FIG. 12 depicts another embodiment of a prosthesis according to the invention, wherein the mechanical restraint element 88 of the release device 16 is designed as a sliding element that interacts with a restraint structure 92. The restraint structure is formed by a surface progression, the surface having a varying distance A from the axis of rotation D.

If the foot part 18 is in its zero position, an ankle torque M must be present on the foot part 18 in order to move the sliding element 88 radially outwards against a spring force of a spring 94. In this position, the sliding element is labelled 88' and drawn with a dotted line.

As long as the ankle torque M lies below the threshold, the sliding element 88 lies flat with a front edge 96 on an incline 98 of the restraint structure, thereby preventing a dorsal extension movement of the foot part 18. However, a plantar flexion movement is still possible and is even supported by the pressure of the spring 94.

In the present case, the foot part 18 comprises a pin 100 around which a coupling ring 102 is arranged. An enclosing structure 104 of the foot part 18 is arranged around the coupling ring 102.

The release device 16 comprises a return element 106, which is formed in the present case by a flap that is fixed on one side only. The mechanical return element 106 is arranged in such a way that a plantar flexion movement PF of the foot part 106 causes the return element to slip through relative to the coupling ring 102. However, a dorsal extension movement DE of the foot part 18 causes the return element 106 to frictionally engage with the coupling ring 102, meaning the coupling ring 102 rotates with it.

The coupling ring 102 comprises a brake 108 that brakes a dorsal extension movement of the foot part 18. The one brake 108, the coupling ring 102 and the return element 106 are connected with one another in such a way that when the foot part 18 carries out a dorsal extension movement, the return element 106 engages with the coupling ring 102 and the brake brakes the dorsal extension movement. If, on the other hand, the foot part 18 carries out a plantar flexion movement, the brake 108 does not brake the plantar flexion movement, or does so less strongly than the dorsal extension movement.

It is possible and represents a preferred embodiment that the restraint structure 92 is fixed, so as to be detachable, relative to the foot part 18 in a radial direction relative to the axis of rotation D. For example, the restraint structure 92 is arranged on a moveable adjustment part that can be determined relative to the foot part 18. In this case, this adjustment part may be initially released from the foot part 19, then swiveled about the axis of rotation D relative to the foot part 18 and then re-attached to the foot part 18. This alters the angle setting at which the foot part 18 is in the zero position. The zero position from which the dorsal extension movement can be impeded to a greater degree can be set in this manner.

REFERENCE LIST 10 prosthesis
12 lower limb attachment part
14 connection element
16 release device
18 foot part
20 lower limb accommodation
21 lower limb
22 foot shell
24 base plate
26 rigid arm
27 second arm
28 partial joint
29 restraint device
30 hydraulic cylinder
31 check valve
32 piston rod
34 cylinder housing
36 fluid
38 ball area
40 outlet
42 interior
44 excess pressure non-return valve
46 adjustable throttle
48 inflow opening
50 outflow opening
52 heel section
54 inflow opening
56 return channel
58 second check valve, non-return valve
59 damping device
60 return flow opening
62 pre-loading device
64 compression spring
66 plate
68 end stop
70 damping device
72 forefoot joint
74 tip of the foot
76 midfoot part
78 return element
80 sequence valve
82 second hydraulic cylinder
84 second piston rod
86 second cylinder housing
88 restraint element
90 recess
92 restraint structure
94 spring
96 front edge
98 incline
100 pin
102 coupling ring
104 enclosing structure
106 return element
108 brake
D axis of rotation
$D_{eff}$ momentary axis of rotation
DF plantar extension direction
DE dorsal extension direction
F force
$F_{stand}$ standing force
M ankle torque
$p_{stand}$ standing pressure
p pressure
$p_{open}$ opening pressure
P arrow

The invention claimed is:

1. A prosthesis, comprising:
a lower limb attachment part;
a foot part;
a connection element with a joint function that connects the lower limb attachment part with the foot part; and
a release device that can be brought into a locking position, in which the foot part and the lower limb attachment part are connected to each other in a rotationally fixed manner at least relative to a dorsal extension movement, and into a release position, in which the foot part can be rotated relative to the lower limb attachment part;
wherein the release device is configured to passively switch from the locking position into the release position when a variable which correlates to an ankle torque in the connection element is above a preset threshold and during a stance phase prior to initiation of a swing phase during a gait cycle.

2. The prosthesis according to claim 1, wherein the release device is configured to passively switch from the locking position into the release position when the variable is the ankle torque and the ankle torque lies above a preset torque threshold.

3. The prosthesis according to claim 2, wherein the release device is configured such that
when the ankle torque lies above the torque threshold, the foot part moves into a dorsally extended position, and
the foot part remains in the dorsally extended position during the swing phase.

4. The prosthesis according to claim 1, wherein the release device comprises:
a first hydraulic cylinder comprising:
a piston rod;
a cylinder housing;
a first end connected to the foot part; and
a second end connected to the lower limb attachment part; and a restraint device configured to:
prevent a movement of the piston rod that leads to the dorsal extension movement of the foot part when the restraint device is in a closing position, and
enable the movement of the piston rod when the restraint device is in an open position.

5. The prosthesis according to claim 4, wherein the restraint device comprises a first check valve configured to:
prevent the movement of the piston rod that leads to the dorsal extension movement of the foot part when the first check valve is in a closing position;
enable the dorsal extension movement of the foot part when the first check valve is in an open position; and
move out of the closing position into the open position at an opening pressure.

6. The prosthesis according to claim 5, wherein the first check valve includes an excess pressure valve, and the torque threshold is set based on the opening pressure of the first check valve at which the excess pressure valve moves the first check valve out of the closing position into the open position.

7. The prosthesis according to claim 5, wherein the restraint device comprises a second check valve configured to:
prevent a plantar flexion movement of the foot part when the second check valve is in a closing position;
enable the plantar flexion movement of the foot part when the second check valve is in an open position;
move the second check valve out of the second check valve closing position into the second check valve open position at a plantar flexion opening pressure.

8. The prosthesis according to claim 7, wherein the first hydraulic cylinder is:
designed to be double-acting;
connected to the restraint device in such a way that the dorsal extension movement of the foot part only effects a flow of hydraulic fluid through the first check valve and the plantar flexion movement of the foot part only effects a flow of the hydraulic fluid through the second check valve.

9. The prosthesis according to claim 7, wherein the release device comprises a second hydraulic cylinder comprising:
a second piston rod and a second cylinder housing;
a first end of the second hydraulic cylinder connected to the foot part;
a second end of the second hydraulic cylinder connected to the lower limb attachment part;
wherein the second hydraulic cylinder is connected to the restraint device and the first hydraulic cylinder such that:
the dorsal extension movement of the foot part effects a flow of hydraulic fluid from the hydraulic cylinder, through the first check valve and into the second hydraulic cylinder, and
the plantar flexion movement of the foot part effects a flow of the hydraulic fluid from the second hydraulic cylinder, through the second check valve and into the first hydraulic cylinder.

10. The prosthesis according to claim 4, wherein the restraint device comprises a mechanical restraint element.

11. The prosthesis according to claim 10, wherein the release device has a restraint structure and a spring, the restraint structure interacting with the restraint element in such a way that a movement of the foot part beyond a neutral position is only possible against the resistance of the spring.

12. The prosthesis according to claim 10, wherein the release device comprises:
a mechanical return element;
a coupling ring;
a brake;
wherein the mechanical return element, coupling ring, and brake are connected to each other in such a way that when the foot part carries out the dorsal extension movement, the return element engages with the coupling ring such that the brake brakes the dorsal extension movement, and that when the foot part carries out a plantar flexion movement, the brake does not brake the plantar flexion movement, or brakes less strongly than the brake applied during the dorsal extension movement.

13. The prosthesis according to claim 1, wherein the release device comprises a damping device, the damping device providing damping of at least one of:
the dorsal extension movement of the connection element, and
a plantar flexion movement of the connection element.

14. The prosthesis according to claim 1, wherein
the foot part can be brought into a neutral position relative to the lower limb attachment part when a person wearing the prosthesis is standing, and into a dorsal extension position, and
the prosthesis comprises a mechanical pre-loading device configured to pre-load the foot part in the dorsal extension position.

15. The prosthesis according to claim 1, wherein the prosthesis is a prosthetic foot comprising the foot part and wherein the connection element forms an ankle joint.

16. The prosthesis according to claim 1, wherein the release device includes an excess pressure valve, wherein the preset threshold is adjusted by changing an opening pressure of the excess pressure valve.

17. The prosthesis according to claim 16, wherein the excess pressure valve includes a pre-tensioning spring, and changing the opening pressure includes adjusting a spring force of the pre-tensioning spring.

18. A prosthesis, comprising:
a lower limb attachment part;
a foot part;
a connection element having a joint function and being connected to the lower limb attachment part and the foot part; and
a release device that is configured to passively switch between a locking position, in which the foot part and the lower limb attachment part are fixed relative to each other at least relative to a dorsal extension movement, and a release position, in which the foot part is rotatable relative to the lower limb attachment part when a variable is above a preset threshold and during a stance phase prior to initiation of a swing phase during a gait cycle, the variable correlating to an ankle torque in the connection element, and the preset threshold is adjustable.

19. The prosthesis according to claim 18, wherein the release device is configured to passively switch from the locking position to the release position when the variable is the ankle torque and the ankle torque lies above a preset torque threshold.

20. The prosthesis according to claim 19, wherein the release device is configured to allow movement of the foot part into a dorsally extended position when the ankle torque lies above the torque threshold, and the foot part remains in the dorsally extended position during a swing phase.

* * * * *